US012753519B2

(12) United States Patent
Dawson et al.

(10) Patent No.: US 12,753,519 B2
(45) Date of Patent: *Oct. 6, 2026

(54) ELECTROCHEMICAL CO-PRODUCTION OF HYDROGEN AND CARBON MONOXIDE

(71) Applicant: Utility Global, Inc., Houston, TX (US)

(72) Inventors: Matthew Dawson, Katy, TX (US); Nicholas Farandos, Bray (IE); Jin Dawson, Katy, TX (US)

(73) Assignee: Utility Global, Inc., Houston, TX (US)

( * ) Notice: Subject to any disclaimer, the term of this patent is extended or adjusted under 35 U.S.C. 154(b) by 526 days.

This patent is subject to a terminal disclaimer.

(21) Appl. No.: 18/483,749

(22) Filed: Oct. 10, 2023

(65) Prior Publication Data

US 2024/0167169 A1 May 23, 2024

Related U.S. Application Data

(60) Provisional application No. 63/427,573, filed on Nov. 23, 2022.

(51) Int. Cl.
*C25B 1/23* (2021.01)
*C07C 1/04* (2006.01)
(Continued)

(52) U.S. Cl.
CPC .................. *C25B 1/23* (2021.01); *C07C 1/04* (2013.01); *C07C 29/1518* (2013.01); *C25B 1/04* (2013.01); *C25B 13/07* (2021.01); *C25B 15/081* (2021.01)

(58) Field of Classification Search
CPC ......... C07C 1/04; C07C 29/1518; C25B 1/23; C25B 1/04; C25B 13/07; C25B 15/081;
(Continued)

(56) References Cited

U.S. PATENT DOCUMENTS 11,655,546 B2 5/2023 Dawson et al.
11,761,096 B2 9/2023 Dawson et al.
(Continued)

FOREIGN PATENT DOCUMENTS

WO WO-2016/205303 A1 12/2016

OTHER PUBLICATIONS

Bian Liuzhen et al: "An all-oxide electrolysis cells for syngas production with tunable H2/CO yield via co-electrolysis of H2O and CO2", Journal of Power Sources, Elsevier, Amsterdam, NL, vol. 482, Sep. 17, 2020 (Sep. 17, 2020), XP086380994, ISSN: 0378-7753, DOI: 10.1016/J.JPOWSOUR.2020.228887 [retrieved on Sep. 17, 2020].

(Continued)

*Primary Examiner* — Jafar F Parsa
(74) *Attorney, Agent, or Firm* — Foley & Lardner LLP

(57) ABSTRACT

Herein discussed is a method of co-producing carbon monoxide and hydrogen comprising: (a) providing an electrochemical reactor having an anode, a cathode, and a mixed-conducting membrane between the anode and the cathode; (b) introducing a first stream to the anode, wherein the first stream comprises a fuel; (c) introducing a second stream to the cathode, wherein the second stream comprises carbon dioxide and water, wherein carbon monoxide is generated from carbon dioxide electrochemically and hydrogen is generated from water electrochemically. In an embodiment, the anode and the cathode are separated by the membrane and are both exposed to reducing environments during the entire time of operation.

19 Claims, 4 Drawing Sheets

(51) Int. Cl.

| | |
|---|---|
| ***C07C 29/151*** | (2006.01) |
| ***C25B 1/04*** | (2021.01) |
| ***C25B 13/07*** | (2021.01) |
| ***C25B 15/08*** | (2006.01) |

(58) Field of Classification Search

CPC ................. C25B 11/033; C25B 11/075; C25B 11/077; C25B 11/081; C25B 11/089; C25B 5/00; C25B 11/091; C25B 13/05; C25B 3/25; B01D 53/326

See application file for complete search history.

(56) References Cited

U.S. PATENT DOCUMENTS

| | | | |
|---|---|---|---|
| 11,761,100 | B2 | 9/2023 | Dawson et al. |
| 11,767,600 | B2 | 9/2023 | Dawson et al. |
| 11,777,126 | B2 | 10/2023 | Farrandos et al. |
| 11,795,551 | B2 | 10/2023 | Dawson et al. |
| 11,795,552 | B2 | 10/2023 | Farandos et al. |
| 2010/0297537 | A1 | 11/2010 | Coors et al. |
| 2015/0118592 | A1 | 4/2015 | Allebrod et al. |
| 2020/0140297 | A1 | 5/2020 | Hall et al. |
| 2020/0144627 | A1 | 5/2020 | Hall et al. |
| 2020/0144628 | A1 | 5/2020 | Hall et al. |
| 2020/0144633 | A1 | 5/2020 | Hall et al. |
| 2020/0144635 | A1 | 5/2020 | Hall et al. |
| 2020/0144646 | A1 | 5/2020 | Hall et al. |
| 2020/0144647 | A1 | 5/2020 | Hall et al. |
| 2020/0144648 | A1 | 5/2020 | Hall et al. |
| 2020/0144653 | A1 | 5/2020 | Hall et al. |
| 2020/0144654 | A1 | 5/2020 | Hall et al. |
| 2020/0156104 | A1 | 5/2020 | Hall et al. |
| 2020/0176803 | A1 | 6/2020 | Hall et al. |
| 2020/0182549 | A1 | 6/2020 | Hall et al. |
| 2020/0227763 | A1 | 7/2020 | Hall et al. |
| 2020/0235409 | A1 | 7/2020 | Hall et al. |
| 2020/0235410 | A1 | 7/2020 | Hall et al. |
| 2020/0255959 | A1 | 8/2020 | Hall et al. |
| 2020/0255962 | A1 | 8/2020 | Hall et al. |
| 2020/0255963 | A1 | 8/2020 | Dawson et al. |
| 2020/0259186 | A1 | 8/2020 | Hall et al. |
| 2020/0303749 | A1 | 9/2020 | Hall et al. |
| 2021/0024425 | A1 | 1/2021 | Dawson et al. |
| 2021/0069786 | A1 | 3/2021 | Hall et al. |
| 2021/0121978 | A1 | 4/2021 | Dawson et al. |
| 2021/0175531 | A1 | 6/2021 | Farandos et al. |
| 2022/0364245 | A1 | 11/2022 | Farandos et al. |
| 2022/0364251 | A1 | 11/2022 | Dawson et al. |
| 2022/0372635 | A1 | 11/2022 | Farandos et al. |
| 2022/0380210 | A1 | 12/2022 | Farandos et al. |
| 2022/0403532 | A1 | 12/2022 | Farandos et al. |
| 2023/0002915 | A1 | 1/2023 | Dawson et al. |
| 2023/0013911 | A1 | 1/2023 | Dawson et al. |
| 2023/0020427 | A1 | 1/2023 | Farandos et al. |
| 2023/0092683 | A1 | 3/2023 | Farandos et al. |
| 2023/0109683 | A1 | 4/2023 | Dawson et al. |
| 2023/0167560 | A1 | 6/2023 | Dawson et al. |
| 2023/0175143 | A1 | 6/2023 | Farandos et al. |
| 2024/0133052 | A1 | 4/2024 | Matthews et al. |
| 2024/0133062 | A1 | 4/2024 | Dawson et al. |
| 2024/0167169 | A1 | 5/2024 | Dawson et al. |
| 2024/0200210 | A1 | 6/2024 | Dawson |
| 2024/0209530 | A1 | 6/2024 | Dawson et al. |
| 2024/0229253 | A9 | 7/2024 | Matthews et al. |
| 2024/0287688 | A1 | 8/2024 | Dawson et al. |
| 2024/0287689 | A1 | 8/2024 | Dawson et al. |
| 2024/0417867 | A1 | 12/2024 | Dawson et al. |
| 2024/0417869 | A1 | 12/2024 | Dawson et al. |
| 2025/0011945 | A1 | 1/2025 | Dawson et al. |
| 2025/0146147 | A1 | 5/2025 | Dawson |
| 2025/0236962 | A1 | 7/2025 | Dawson et al. |
| 2025/0347480 | A1 | 11/2025 | Kelley et al. |
| 2026/0055518 | A1 | 2/2026 | Dana et al. |
| 2026/0100384 | A1 | 4/2026 | Dawson |
| 2026/0125811 | A1 | 5/2026 | Farandos et al. |

OTHER PUBLICATIONS

International Search Report and Written Opinion for PCT/US2023/076424 dated Feb. 5, 2024.

ELECTROCHEMICAL CO-PRODUCTION OF HYDROGEN AND CARBON MONOXIDE

CROSS-REFERENCE TO RELATED APPLICATIONS

This application claims the benefit under 35 U.S.C. 119(e) of U.S. Provisional Patent Application No. 63/427,573 filed Nov. 23, 2022, the entire disclosure of which is hereby incorporated herein by reference.

TECHNICAL FIELD

This invention generally relates to co-production of hydrogen ($H_2$) and carbon monoxide (CO). More specifically, this invention relates to electrochemical co-production of hydrogen ($H_2$) and carbon monoxide (CO).

BACKGROUND

Carbon monoxide (CO) is a colorless, odorless, tasteless, and flammable gas that is slightly less dense than air. It is well known for its poisoning effect because CO readily combines with hemoglobin to produce carboxyhemoglobin, which is highly toxic when the concentration exceeds a certain level. However, CO is a key ingredient in many chemical and industrial processes. CO has a wide range of functions across all disciplines of chemistry, e.g., metal-carbonyl catalysis, radical chemistry, cation and anion chemistries. Carbon monoxide is a strong reductive agent and has been used in pyrometallurgy to reduce metals from ores for centuries. As an example for making specialty compounds, CO is used in the production of vitamin A.

Hydrogen ($H_2$) in large quantities is needed in the petroleum and chemical industries. For example, large amounts of hydrogen are used in upgrading fossil fuels and in the production of methanol or hydrochloric acid. Petrochemical plants need hydrogen for hydrocracking, hydrodesulfurization, hydrodealkylation. Hydrogenation processes to increase the level of saturation of unsaturated fats and oils also need hydrogen. Hydrogen is also a reducing agent of metallic ores. Hydrogen may be produced from electrolysis of water, steam reforming, lab-scale metal-acid process, thermochemical methods, or anaerobic corrosion. Many countries are aiming at a hydrogen economy.

In the Fischer-Tropsch process, CO and $H_2$ are both essential building blocks, which are often produced by converting carbon-rich feedstocks (e.g., coal). A mixture of CO and $H_2$—syngas—can combine to produce various liquid fuels, e.g., via the Fischer-Tropsch process. Syngas can also be converted to lighter hydrocarbons, methanol, ethanol, or plastic monomers (e.g., ethylene). The ratio of $CO/H_2$ is important in all such processes in order to produce the desired compounds. Conventional techniques require extensive and expensive separation and purification processes to obtain the CO and $H_2$ as building blocks.

Clearly there is increasing need and interest to develop new technological platforms to produce these building blocks and valuable products. This disclosure discusses co-production of CO and $H_2$ via efficient electrochemical pathways. Furthermore, the method and system as disclosed herein do not require the extensive and expensive separation and purification processes as needed in traditional technologies.

SUMMARY

Herein discussed is a method of co-producing carbon monoxide and hydrogen comprising: (a) providing an electrochemical reactor having an anode, a cathode, and a mixed-conducting membrane between the anode and the cathode; (b) introducing a first stream to the anode, wherein the first stream comprises a fuel; (c) introducing a second stream to the cathode, wherein the second stream comprises carbon dioxide and water, wherein carbon monoxide is generated from carbon dioxide electrochemically and hydrogen is generated from water electrochemically. In various embodiments, the second stream comprises hydrogen or carbon monoxide additionally to ensure a true reducing environment for the cathode throughout the operation of the reactor.

In an embodiment, the anode and the cathode are separated by the membrane and are both exposed to reducing environments during the entire time of operation. In an embodiment, the cathode comprises Ni or NiO and a material selected from the group consisting of YSZ, CGO, SDC, SSZ, LSGM, CoCGO, and combinations thereof. In an embodiment, the anode and the cathode and the membrane have the same elements. In an embodiment, the anode and the cathode and the membrane comprise Ni—YSZ or LaSrFeCr—SSZ or LaSrFeCr—SCZ or LST-SCZ.

In an embodiment, the anode comprises Ni or NiO and a material selected from the group consisting of YSZ, CGO, SDC, SSZ, LSGM, CoCGO, and combinations thereof. In an embodiment, the fuel comprises ammonia, syngas, hydrogen, methanol, carbon monoxide, or In an embodiment, the anode is liquid during operation. In an embodiment, the anode comprises tin (Sn), bismuth (Bi), cadmium (Cd), lead (Pb), antimony (Sb), indium (In), silver (Ag), babbitt metal, or combinations thereof. In an embodiment, the anode comprises lithium carbonate, potassium carbonate, sodium carbonate, or combinations thereof. In an embodiment, the fuel comprises carbon, ammonia, syngas, hydrogen, methanol, carbon monoxide, a hydrocarbon, biodiesel, renewable natural gas, biogas, biomass, biowaste, charcoal, petcoke, cooking oil, or combinations thereof.

In an embodiment, the anode comprises doped or undoped ceria and a material selected from the group consisting of Cu, CuO, CuzO, Ag, $Ag_2O$, Au, $Au_2O$, $Au_2O_3$, Pt, Pd, Ru, Rh, Ir, LaCaCr, LaSrCrFe, YSZ, CGO, SDC, SSZ, LSGM, stainless steel, and combinations thereof. In an embodiment, the fuel comprises a hydrocarbon.

In an embodiment, the membrane comprises an electronically conducting phase and an ionically conducting phase. In an embodiment, the electronically conducting phase comprises doped lanthanum chromite or an electronically conductive metal or combination thereof; and wherein the ionically conducting phase comprises a material selected from the group consisting of gadolinium or samarium doped ceria, yttria-stabilized zirconia (YSZ), lanthanum strontium gallate magnesite (LSGM), scandia-stabilized zirconia (SSZ), Sc and Ce doped zirconia (SCZ), and combinations thereof.

In an embodiment, the membrane comprises CoCGO or LST (lanthanum-doped strontium titanate)-stabilized zirconia. In an embodiment, the stabilized zirconia comprises YSZ or SSZ or SCZ (scandia-ceria-stabilized zirconia). In an embodiment, the LST comprises $LaSrCaTiO_3$. In an embodiment, the membrane comprises Nickel, Copper, Cobalt, or Niobium-doped zirconia.

In an embodiment, the cathode exhaust is passed through a separator, wherein the generated carbon monoxide and hydrogen are separated from the exhaust. In an embodiment, the method comprises utilizing the separated CO and $H_2$ to produce methanol, ethanol, hydrocarbons, plastic monomers, polyethylene, or combinations thereof. In an embodiment, the reactor comprises no interconnect and no current collector. In an embodiment, the reactor produces no electricity and receives no electricity.

Further aspects and embodiments are provided in the following drawings, detailed description, and claims. Unless specified otherwise, the features as described herein are combinable and all such combinations are within the scope of this disclosure.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Overview

Figure 1A:
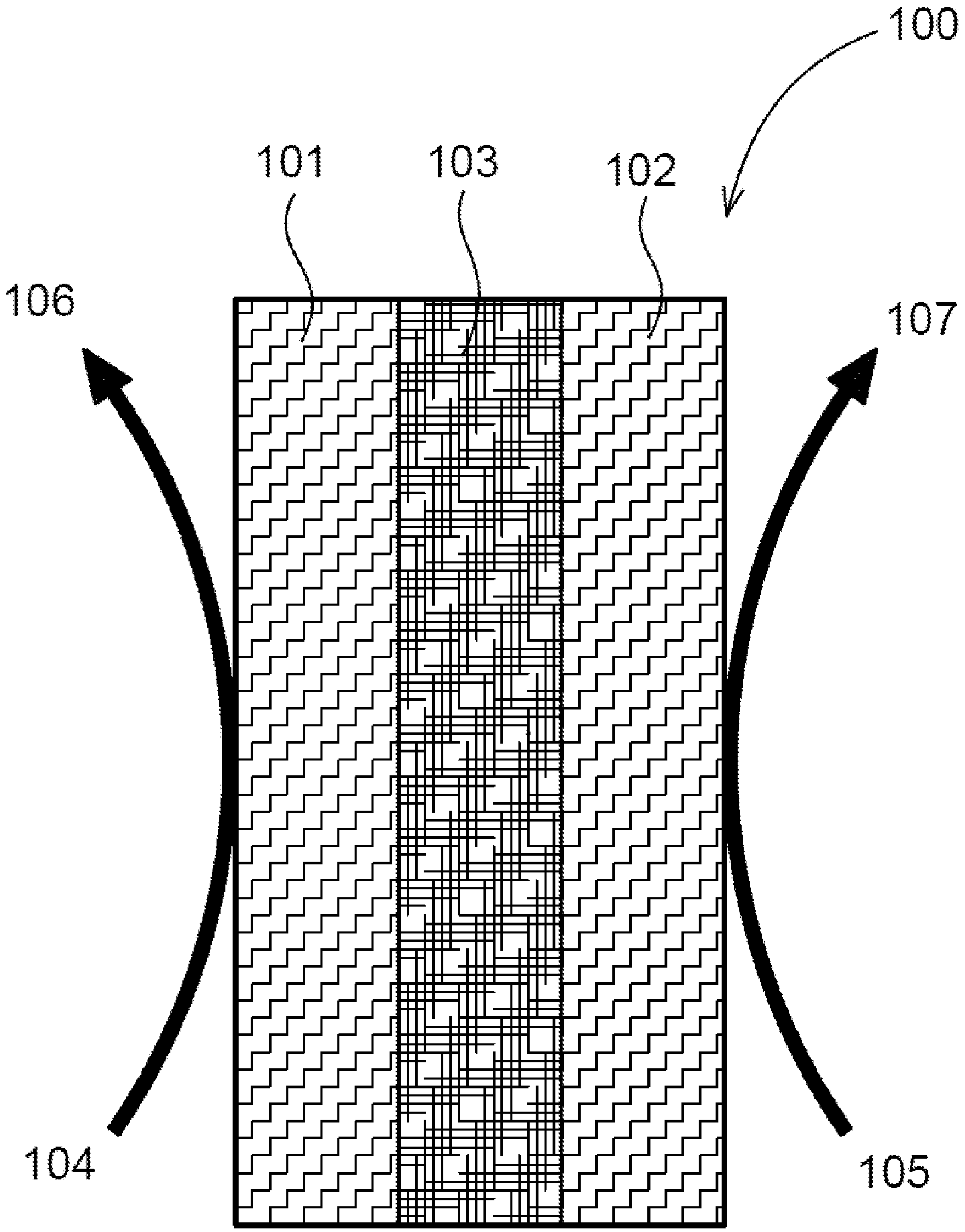
FIG. 1A illustrates an electrochemical (EC) reactor or an electrochemical gas producer, according to an embodiment of this disclosure.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like. As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, compositions and materials are used interchangeably unless otherwise specified. Each composition/material may have multiple elements, phases, and components. Heating as used herein refers to actively adding energy to the compositions or materials.

As used herein, YSZ refers to yttria-stabilized zirconia; SDC refers to samaria-doped ceria; SSZ refers to scandia-stabilized zirconia; LSGM refers to lanthanum strontium gallate magnesite.

In this disclosure, no substantial amount of $H_2$ means that the volume content of the hydrogen is no greater than 5%, or no greater than 3%, or no greater than 2%, or no greater than 1%, or no greater than 0.5%, or no greater than 0.1%, or no greater than 0.05%.

As used herein, CGO refers to Gadolinium-Doped Ceria, also known alternatively as gadolinia-doped ceria, gadolinium-doped cerium oxide, cerium(IV) oxide, gadolinium-doped, GDC, or GCO, (formula $Gd:CeO_2$). CGO and GDC are used interchangeably unless otherwise specified. Syngas (i.e., synthesis gas) in this disclosure refers to a mixture consisting primarily of hydrogen, carbon monoxide and carbon dioxide.

A mixed conducting membrane is able to transport both electrons and ions. Ionic conductivity includes ionic species such as oxygen ions (or oxide ions), protons, halogenide anions, chalcogenide anions. In various embodiment, the mixed conducting membrane of this disclosure comprises an electronically conducting phase and an ionically conducting phase.

In this disclosure, the axial cross section of the tubulars is shown to be circular, which is illustrative only and not limiting. The axial cross section of the tubulars is any suitable shape as known to one skilled in the art, such as square, square with rounded corners, rectangle, rectangle with rounded corners, triangle, hexagon, pentagon, oval, irregular shape, etc.

As used herein, ceria refers to cerium oxide, also known as ceric oxide, ceric dioxide, or cerium dioxide, is an oxide of the rare-earth metal cerium. Doped ceria refers to ceria doped with other elements, such as samaria-doped ceria (SDC), or gadolinium-doped ceria (GDC or CGO). As used herein, chromite refers to chromium oxides, which includes all the oxidation states of chromium oxides.

A layer or substance being impermeable as used herein refers to it being impermeable to fluid flow. For example, an impermeable layer or substance has a permeability of less than 1 micro darcy, or less than 1 nano darcy.

In this disclosure, sintering refers to a process to form a solid mass of material by heat or pressure, or a combination thereof, without melting the material to the extent of liquefaction. For example, material particles are coalesced into a solid or porous mass by being heated, wherein atoms in the material particles diffuse across the boundaries of the particles, causing the particles to fuse together and form one solid piece.

The term "in situ" in this disclosure refers to the treatment (e.g., heating or cracking) process being performed either at the same location or in the same device. For example, ammonia cracking taking place in the electrochemical reactor at the anode is considered in situ.

Electrochemistry is the branch of physical chemistry concerned with the relationship between electrical potential, as a measurable and quantitative phenomenon, and identifiable chemical change, with either electrical potential as an outcome of a particular chemical change, or vice versa. These reactions involve electrons moving between electrodes via an electronically-conducting phase (typically, but not necessarily, an external electrical circuit), separated by an ionically-conducting and electronically insulating membrane (or ionic species in a solution). When a chemical reaction is effected by a potential difference, as in electrolysis, or if electrical potential results from a chemical reaction as in a battery or fuel cell, it is called an electrochemical reaction. Unlike chemical reactions, in electrochemical reactions electrons (and necessarily resulting ions), are not transferred directly between molecules, but via the aforementioned electronically conducting and ionically conducting circuits, respectively. This phenomenon is what distinguishes an electrochemical reaction from a chemical reaction.

Related to the electrochemical reactor and methods of use, various components of the reactor are described such as electrodes and membranes along with materials of construction of the components. The following description recites various aspects and embodiments of the inventions disclosed herein. No particular embodiment is intended to define the scope of the invention. Rather, the embodiments provide non-limiting examples of various compositions and methods that are included within the scope of the claimed inventions. The description is to be read from the perspective of one of ordinary skill in the art. Therefore, information that is well-known to the ordinarily skilled artisan is not necessarily included.

An interconnect in an electrochemical device (e.g., a fuel cell) is often either metallic or ceramic that is placed between the individual cells or repeat units. Its purpose is to connect each cell or repeat unit so that electricity can be distributed or combined. An interconnect is also referred to as a bipolar plate in an electrochemical device. An interconnect being an impermeable layer as used herein refers to it being a layer that is impermeable to fluid flow.

Electrochemical Reactor

Contrary to conventional practice, an electrochemical reactor has been discovered, which comprises an ionically conducting membrane, wherein the reactor is capable of reforming a hydrocarbon electrochemically or of performing water gas shift reactions electrochemically. The electrochemical reforming reactions involve the exchange of an ion through the membrane to oxidize the hydrocarbon. The electrochemical reactions involve the exchange of an ion through the membrane and include forward water gas shift reactions, or reverse water gas shift reactions, or both. These are different from traditional reforming reactions and water gas shift reactions via chemical pathways because they involve direct combination of reactants.

FIG. 1A illustrates an electrochemical reactor or an electrochemical (EC) gas producer 100, according to an embodiment of this disclosure. electrochemical reactor (or EC gas producer) device 100 comprises first electrode 101, membrane 103 a second electrode 102. First electrode 101 is configured to receive a fuel 104. For example, stream 104 comprises $H_2$, ammonia, syngas, or combinations thereof. Stream 104 contains no oxygen. Second electrode 102 is configured to receive a stream 105 that contains carbon dioxide ($CO_2$) and water ($H_2O$).

In an embodiment, device 100 is configured to receive $CO_2$ and $H_2O$ and to generate CO and $H_2$ contained in stream 107 at the second electrode (102). In some cases, the second electrode also receives a small amount of CO or $H_2$ or both. Since $CO_2$ and $H_2O$ provides the oxide ion (which is transported through the membrane) needed to oxidize the fuel at the opposite electrode, $CO_2$ and $H_2O$ are considered the oxidant in this scenario. The reduction of $CO_2$ produces CO. The reduction of $H_2O$ produces $H_2$. As such, the first electrode 101 is performing oxidation reactions in a reducing environment; the second electrode 102 is performing reduction reactions in a reducing environment. In some cases, such environments are considered nominally reducing environments. In various embodiments, both electrodes are exposed to reducing environments during the entire time of operation.

In various embodiments, 103 represents an oxide ion conducting membrane. In an embodiment, the first electrode 101 and the second electrode 102 comprise Ni—YSZ or NiO—YSZ. In an embodiment, the oxide ion conducting membrane 103 also conducts electrons. In various embodiments, electrodes 101 and 102 comprise Ni or NiO and a material selected from the group consisting of YSZ, CGO, SDC, SSZ, LSGM, CoCGO, and combinations thereof. Alternatively, gases containing a hydrocarbon are reformed before coming into contact with the membrane 103/electrode 101. The reformer is configured to perform steam reforming, dry reforming, or combination thereof. The reformed gases are suitable as feed stream 104.

In an embodiment, the anode and the cathode and the membrane have the same elements. For example, the anode and the cathode and the membrane comprise Ni—YSZ. In an embodiment, the anode and the cathode and the membrane comprise LaSrFeCr (Lanthanum Strontium Iron doped Chromite)—SSZ (Scandia stabilized Zirconia). In an embodiment, the anode and the cathode and the membrane comprise LaSrFeCr—SCZ (Sc and Ce stabilized zirconia). In an embodiment, the anode and the cathode and the membrane comprise LST (lanthanum-doped strontium titanate)-SCZ.

In this disclosure, no oxygen means there is no oxygen present at first electrode 101 or at least not enough oxygen that would interfere with the reaction. Also, in this disclosure, water only means that the intended feedstock is water and does not exclude trace elements or inherent components in water. For example, water containing salts or ions is considered to be within the scope of water only. Water only also does not require 100% pure water but includes this embodiment.

In various embodiments, the device does not contain a current collector. In an embodiment, the device comprises no interconnect. There is no need for electricity and such a device is not an electrolyzer. This is a major advantage of the EC reactor of this disclosure. The membrane 103 is configured to conduct electrons and as such is mixed conducting, i.e., both electronically conductive and ionically conductive. In an embodiment, the membrane 103 conducts oxide ions and electrons. In an embodiment, the electrodes 101, 102 and the membrane 103 are tubular (see, e.g., FIGS. 2A and 2B). In an embodiment, the electrodes 101, 102 and the membrane 103 are planar. In these embodiments, the electrochemical reactions at the electrodes are spontaneous without the need to apply potential/electricity to the reactor.

In an embodiment, the electrochemical reactor (or EC gas producer) is a device comprising a first electrode, a second electrode, and a membrane between the electrodes, wherein the first electrode and the second electrode comprise a metallic phase that does not contain a platinum group metal when the device is in use, and wherein the membrane is oxide ion conducting. In an embodiment, the first electrode is configured to receive a fuel. In an embodiment, said fuel comprises ammonia, syngas, hydrogen, methanol, carbon monoxide, or combinations thereof. In an embodiment, the second electrode is configured to receive $CO_2$ and $H_2O$ (with a small amount of CO or $H_2$ or both) and configured to reduce the $CO_2$ to CO and to reduce the $H_2O$ to $H_2$. In various embodiments, such reductions take place electrochemically.

Figure 1B:
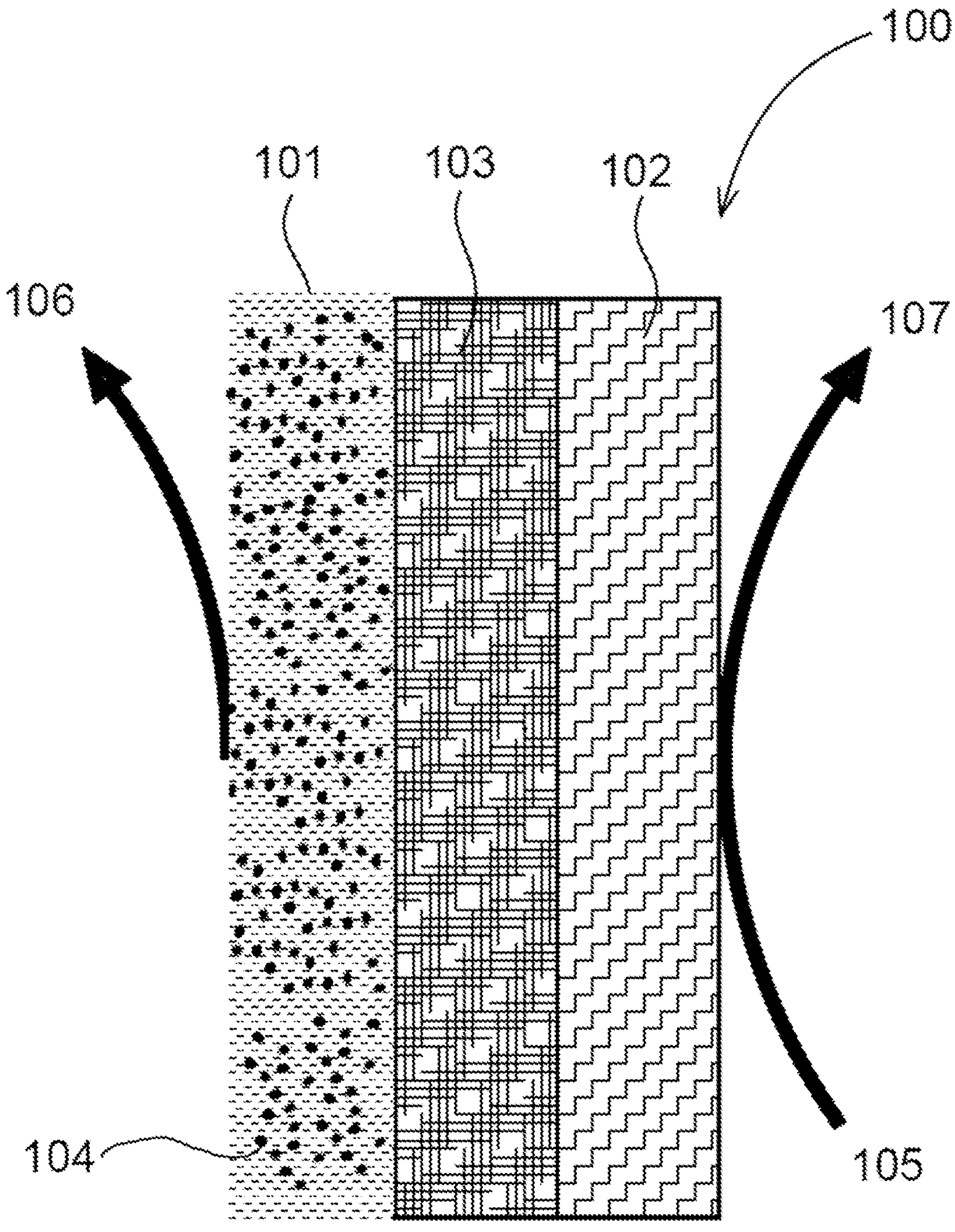
FIG. 1B illustrates an electrochemical (EC) reactor or an electrochemical gas producer, according to an alternative embodiment of this disclosure.

FIG. 1B illustrates an electrochemical reactor or an electrochemical (EC) producer 100 for hydrogen and carbon monoxide co-production, according to an embodiment of this disclosure. The EC reactor 100 comprises a first electrode 101, membrane 103, and a second electrode 102. First electrode 101, in various embodiments, is a metal or carbonate that is configured to carry, suspend, or circulate feedstock 104 when the reactor is in operation, wherein the metal or carbonate becomes liquid. The metal comprises tin (Sn), bismuth (Bi), cadmium (Cd), lead (Pb), antimony (Sb), indium (In), silver (Ag), babbitt metal, or combinations thereof. The carbonate comprises lithium carbonate, potassium carbonate, sodium carbonate, or combinations thereof.

Feedstock 104 comprises carbon, ammonia, syngas, hydrogen, methanol, carbon monoxide, a hydrocarbon, biodiesel, renewable natural gas, biogas, biomass, biowaste, charcoal, petcoke, cooking oil, or combinations thereof. Carbon may be obtained from any source known to one skilled in the art, such as petroleum coke (coke or petcoke), carbon black, char, graphite, coal, biowaste, biomass. Examples of a hydrocarbon are methane, ethane, propane, butane. In various embodiments, the volume content of solid feedstock (e.g., carbon) in the first electrode is no greater than 30 vol %. At the first electrode 101, feedstock 104 is oxidized via the oxide ions transported through the membrane 103. For example, carbon is converted to carbon monoxide or carbon dioxide (i.e., carbon oxides). Stream 106 represents exhaust from the first electrode.

Second electrode 102 is configured to receive water (e.g., steam) and carbon dioxide as denoted by 105. In an embodiment, stream 105 also contains hydrogen or carbon monoxide or both. At the second electrode 102, water is electrochemically reduced to hydrogen and carbon dioxide is electrochemically reduced to carbon monoxide. Stream 107 represents exhaust from the second electrode. Since water or carbon dioxide provides the oxide ion (which is transported through the membrane) needed to oxidize the feedstock at the opposite electrode, water or carbon dioxide is considered the oxidant in this scenario. As such, the first electrode 101 is performing oxidation reactions in a reducing environment; the second 102 electrode is performing reduction reactions in a reducing environment. In an embodiment, the second electrode 102 comprise Ni—YSZ or NiO-YSZ. In various embodiments, electrode 102 comprise Ni or NiO and a material selected from the group consisting of YSZ, CGO, SDC, SSZ, LSGM, CoCGO, and combinations thereof. In various embodiments, both electrodes are exposed to reducing environments during the entire time of operation.

In various embodiments, 103 represents an oxide ion conducting membrane. In an embodiment, the oxide ion conducting membrane 103 also conducts electrons. Therefore, the reactor does not contain a current collector or an interconnect. There is no need for electricity and such a reactor is not an electrolyzer. This is a major advantage of the EC reactor of this disclosure. The membrane 103 is configured to conduct electrons and as such is mixed conducting, i.e., both electronically conductive and ionically conductive. In an embodiment, the membrane 103 conducts oxide ions and electrons. In these embodiments, the electrochemical reactions at the anode and the cathode are spontaneous without the need to apply potential/electricity to the reactor.

In an embodiment, the membrane comprises an electronically conducting phase containing doped lanthanum chromite or an electronically conductive metal or combination thereof; and wherein the membrane comprises an ionically conducting phase containing a material selected from the group consisting of gadolinium doped ceria (CGO), samarium doped ceria (SDC), yttria-stabilized zirconia (YSZ), lanthanum strontium gallate magnesite (LSGM), scandia-stabilized zirconia (SSZ), Sc and Ce doped zirconia, Cobalt-doped gadolinium-doped ceria (CoCGO), and combinations thereof. In an embodiment, the doped lanthanum chromite comprises strontium doped lanthanum chromite, iron doped lanthanum chromite, strontium and iron doped lanthanum chromite, lanthanum calcium chromite, or combinations thereof; and wherein the conductive metal comprises Ni, Cu, Ag, Au, Pt, Rh, or combinations thereof.

In an embodiment, the membrane comprises an electronically conducting phase and an ionically conducting phase. In some cases, the electronically conducting phase comprises doped lanthanum chromite or an electronically conductive metal or combination thereof; and wherein the ionically conducting phase comprises a material selected from the group consisting of gadolinium or samarium doped ceria, yttria-stabilized zirconia (YSZ), lanthanum strontium gallate magnesite (LSGM), scandia-stabilized zirconia (SSZ), Sc and Ce doped zirconia (SCZ), and combinations thereof. In an embodiment, the membrane comprises CoCGO or LST (lanthanum-doped strontium titanate)-stabilized zirconia. In an embodiment, the stabilized zirconia comprises YSZ or SSZ or SCZ (scandia-ceria-stabilized zirconia). In an embodiment, the LST comprises $LaSrCaTiO_3$. In an embodiment, the membrane comprises Nickel, Copper, Cobalt, or Niobium-doped zirconia.

In an embodiment, the membrane comprises cobalt-CGO (CoCGO), i.e., cobalt doped CGO. In an embodiment, the membrane consists essentially of CoCGO. In an embodiment, the membrane consists of CoCGO. In an embodiment, the membrane comprises LST (lanthanum-doped strontium titanate)-YSZ or LST-SSZ or LST-SCZ (scandia-ceria-stabilized zirconia). In an embodiment, the membrane consists essentially of LST-YSZ or LST-SSZ or LST-SCZ. In an embodiment, the membrane consists of LST-YSZ or LST-SSZ or LST-SCZ. In this disclosure, LST-YSZ refers to a composite of LST and YSZ. In various embodiments, the LST phase and the YSZ phase percolate each other. In this disclosure, LST-SSZ refers to a composite of LST and SSZ. In various embodiments, the LST phase and the SSZ phase percolate each other. In this disclosure, LST-SCZ refers to a composite of LST and SCZ. In various embodiments, the LST phase and the SCZ phase percolate each other. YSZ, SSZ, and SCZ are types of stabilized zirconia's.

Figure 2A:
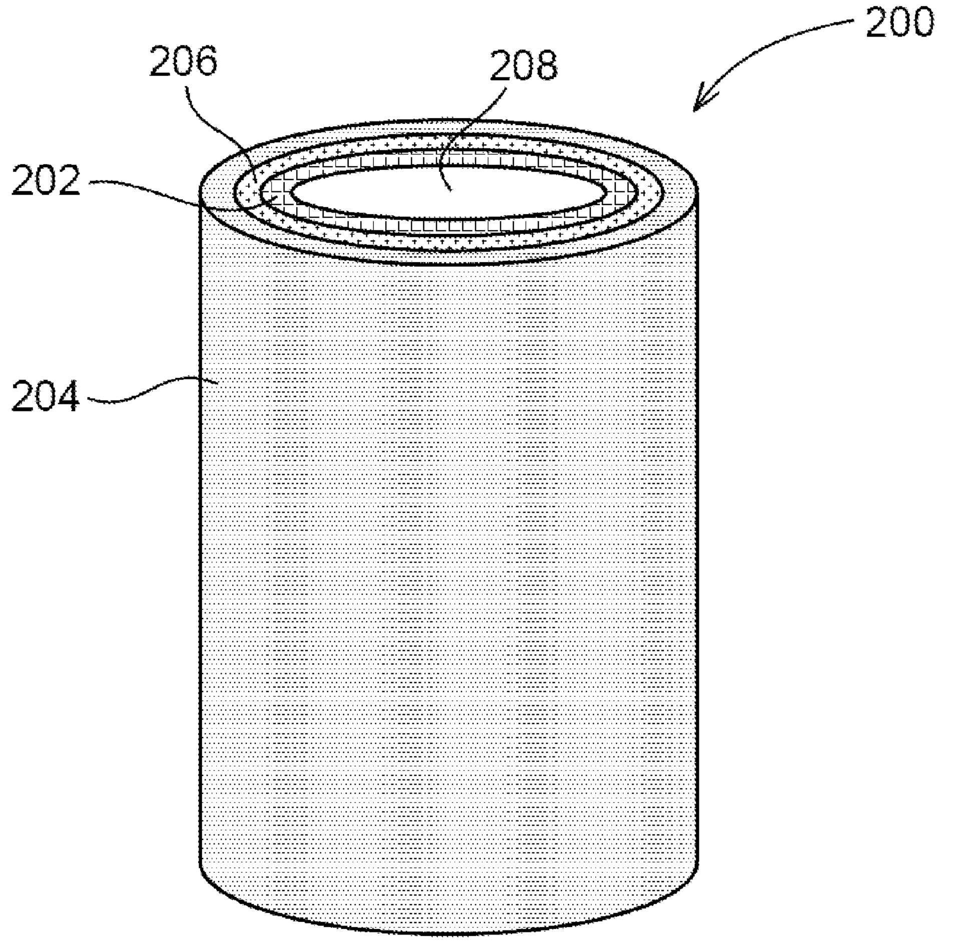
FIG. 2A illustrates a tubular electrochemical reactor, according to an embodiment of this disclosure.
Figure 2B:
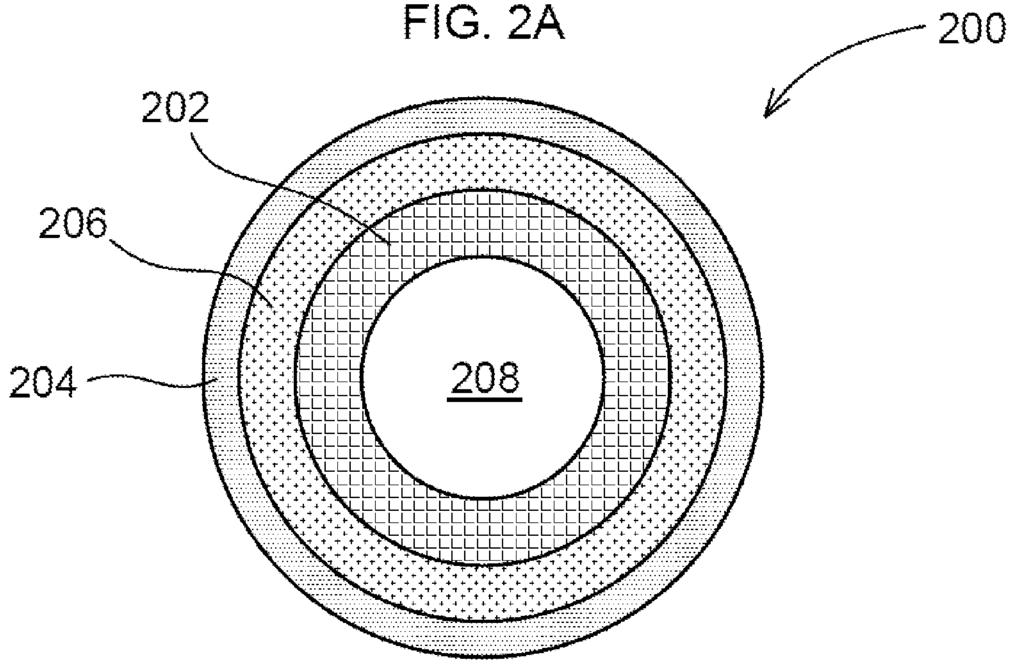
FIG. 2B illustrates a cross section of a tubular electrochemical reactor, according to an embodiment of this disclosure.

FIG. 2A illustrates (not to scale) a tubular electrochemical (EC) reactor or an EC gas producer 200, according to an embodiment of this disclosure. Tubular producer 200 includes an inner tubular structure 202, an outer tubular structure 204, and a membrane 206 disposed between the inner and outer tubular structures 202, 204, respectively. Tubular producer 200 further includes a void space 208 for fluid passage. FIG. 2B illustrates (not to scale) a cross section of a tubular producer 200, according to an embodiment of this disclosure. Tubular producer 200 includes a first inner tubular structure 202, a second outer tubular structure 204, and a membrane 206 between the inner and outer tubular structures 202, 204. Tubular producer 200 further includes a void space 208 for fluid passage.

In an embodiment, the electrodes and the membrane are tubular with the first electrode being outermost and the second electrode being innermost, wherein the second electrode is configured to receive $H_2O$ and $CO_2$. In an embodiment, the electrodes and the membrane are tubular with the first electrode being innermost and the second electrode being outermost, wherein the second electrode is configured to receive $H_2O$ and $CO_2$. In an embodiment, the electrodes and the membrane are planar.

The electrochemical reactions taking place in the reactor comprise electrochemical half-cell reactions. In various embodiments, the half-cell reactions take place at triple phase boundaries, wherein the triple phase boundaries are the intersections of pores with the electronically conducting phase and the ionically conducting phase.

In various embodiments, the ionically conducting membrane conducts protons or oxide ions. In various embodiments, the ionically conducting membrane comprises solid oxide. In various embodiments, the ionically conducting membrane is impermeable to fluid flow. In various embodiments, the ionically conducting membrane also conducts electrons and wherein the reactor comprises no interconnect.

Electrochemical Co-Production of $H_2$ and CO

The EC reactor as discussed above is suitable to electrochemically produce CO from $CO_2$ and $H_2$ from $H_2O$ simultaneously on the cathode side. In an embodiment, the reactor comprises porous electrodes that comprise metallic phase and ceramic phase, wherein the metallic phase is electronically conductive and wherein the ceramic phase is ionically conductive. In various embodiments, the electrodes have no current collector attached to them. In various embodiments, the reactor does not contain any current collector or interconnect. Clearly, such a reactor is fundamentally different from any electrolysis device or any fuel cell.

Figure 3:
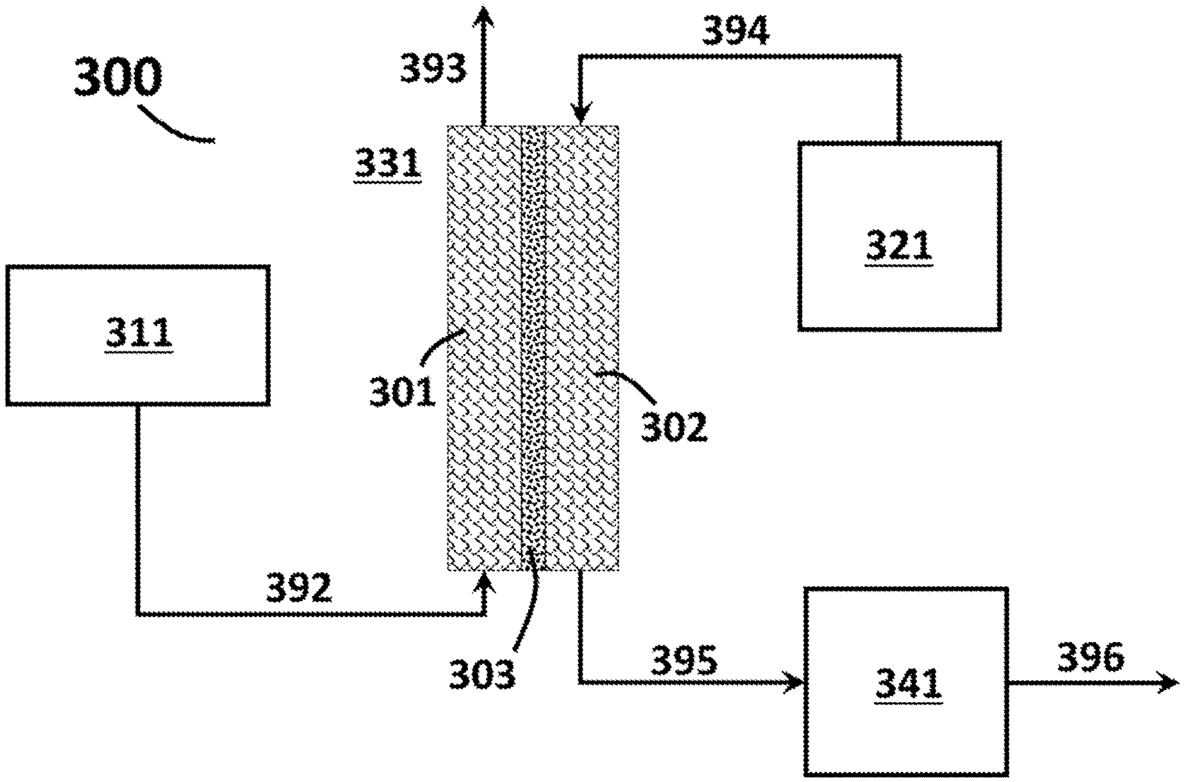
FIG. 3 illustrates a CO and $H_2$ co-production system having an electrochemical reactor, according to an embodiment of this disclosure.

As illustrated in FIG. 3, a co-production system (300) for CO and $H_2$ is shown. The system 300 comprises an EC reactor 331, a fuel source 311, a carbon dioxide and water source 321, and a separator 341. 301 represents the anode in the reactor and 302 represents the cathode in the reactor. 303 represents the membrane between the electrodes in the reactor. A first stream 392 comprising a fuel is passed through the anode 301, becomes oxidized, and exits the anode as stream 393. A second stream 394 from source 321 is passed through the cathode 302, wherein $CO_2$ is reduced to CO and $H_2O$ is reduced to $H_2$. Cathode exhaust stream 395 is passed through the separator 341, wherein CO is separated from $CO_2$ and $H_2$ is separated from $H_2O$. Product stream 396 exits the separator 341 and consists essentially of CO and $H_2$. A portion of stream 395 or of stream 396 may be recycled to the cathode 302 (not shown in FIG. 3). In various embodiments, the cathode receives hydrogen or carbon monoxide in addition to steam and carbon dioxide to ensure a true reducing environment throughout the operation of the reactor. In various embodiments, both electrodes are exposed to reducing environments during the entire time of operation.

The process and system of CO and $H_2$ co-production according to this disclosure have various advantages. CO generation from $CO_2$ is desirable because it reduces greenhouse gas emission. Making CO and $H_2$ locally (on site) is inherently safer than transporting CO and $H_2$ in pressurized containers or vessels. The process of this disclosure utilizes efficient electrochemical pathways but yet needs no electricity. The CO/$CO_2$ and $H_2$/$H_2O$ separation from the cathode exhaust is easy and inexpensive. As such, the method and system of this disclosure are cost competitive both in capital equipment and in operational expenses.

In various embodiments, the ratio of $H_2$/CO co-production is controlled by varying the input ratio of $H_2O$/$CO_2$, by varying the operation temperature, by varying the fuel composition, or combinations thereof. As such, the product from the separator is suitable for various downstream chemical productions without the need for further purification or modification. This is another major advantage of the process and system of this disclosure.

Production of Valuable Products

The production system 300 may further comprise a chemical producer (not shown in FIG. 3) selected from the group consisting of Fischer-Tropsch reactor, methanol producer, ethanol producer, hydrocarbon producer, plastic monomer producer, and combinations thereof. The Fischer-Tropsch reactor is able to generate valuable products such as naphtha, gasoline, diesel, wax. The produced methanol may be further converted to gasoline, ethylene, acetic acid, formaldehyde, methyl acetate, polyolefins, dimethyl ether (DME), or combinations thereof. In various embodiments, the chemical producer is configured to receive carbon monoxide and hydrogen from the separator. Additionally, the system may comprise a polymerization unit to convert the plastic monomers to various types of plastics. The configurations and arrangements for utilizing the produced CO and $H_2$ are known to one skilled in the art, and all such configurations and arrangements are within the scope of this disclosure.

It is to be understood that this disclosure describes exemplary embodiments for implementing different features, structures, or functions of the invention. Exemplary embodiments of components, arrangements, and configurations are described to simplify the present disclosure; however, these exemplary embodiments are provided merely as examples and are not intended to limit the scope of the invention. The embodiments as presented herein may be combined unless otherwise specified. Such combinations do not depart from the scope of the disclosure.

Additionally, certain terms are used throughout the description and claims to refer to particular components or steps. As one skilled in the art appreciates, various entities may refer to the same component or process step by different names, and as such, the naming convention for the elements described herein is not intended to limit the scope of the invention. Further, the terms and naming convention used herein are not intended to distinguish between components, features, and/or steps that differ in name but not in function.

While the disclosure is susceptible to various modifications and alternative forms, specific embodiments thereof are shown by way of example in the drawings and description. It should be understood, however, that the drawings and detailed description are not intended to limit the disclosure to the particular form disclosed, but on the contrary, the intention is to cover all modifications, equivalents and alternatives falling within the spirit and scope of this disclosure.

What is claimed is:

1. A method of co-producing carbon monoxide and hydrogen comprising: (a) providing an electrochemical reactor having an anode, a cathode, and a mixed-conducting membrane between the anode and the cathode; (b) introducing a first stream to the anode, wherein the first stream comprises a fuel; (c) introducing a second stream to the cathode, wherein the second stream comprises carbon dioxide and water and additionally hydrogen or carbon monoxide or both, wherein carbon monoxide is generated from carbon dioxide electrochemically and hydrogen is generated from water electrochemically, wherein the reactor produces no electricity and receives no electricity.

2. The method of claim 1, wherein the anode and the cathode are separated by the membrane and are both exposed to reducing environments during the entire time of operation.

3. The method of claim 1, wherein the cathode comprises Ni or NiO and a material selected from the group consisting of YSZ, CGO, SDC, SSZ, LSGM, CoCGO, and combinations thereof.

4. The method of claim 1, wherein the anode and the cathode and the membrane have the same elements.

5. The method of claim 4, wherein the anode and the cathode and the membrane comprise Ni-YSZ or LaSrFeCr-SSZ or LaSrFeCr-SCZ or LST-SCZ.

6. The method of claim 1, wherein the anode comprises Ni or NiO and a material selected from the group consisting of YSZ, CGO, SDC, SSZ, LSGM, CoCGO, and combinations thereof.

7. The method of claim 6, wherein the fuel comprises ammonia, syngas, hydrogen, methanol, carbon monoxide, or combinations thereof.

8. The method of claim 1, wherein the anode is liquid during operation;

wherein the anode comprises tin (Sn), bismuth (Bi), cadmium (Cd), lead (Pb), antimony (Sb), indium (In), silver (Ag), babbitt metal, or combinations thereof or wherein the anode comprises lithium carbonate, potassium carbonate, sodium carbonate, or combinations thereof.

9. The method of claim 8, wherein the fuel comprises carbon, ammonia, syngas, hydrogen, methanol, carbon monoxide, a hydrocarbon, biodiesel, renewable natural gas, biogas, biomass, biowaste, charcoal, petcoke, cooking oil, or combinations thereof.

10. The method of claim 1, wherein the anode comprises doped or undoped ceria and a material selected from the group consisting of Cu, CuO, $Cu_2O$, Ag, $Ag_2O$, Au, $Au_2O$, $Au_2O_3$, Pt, Pd, Ru, Rh, Ir, LaCaCr, LaSrCrFe, YSZ, CGO, SDC, SSZ, LSGM, stainless steel, and combinations thereof.

11. The method of claim 10, wherein the fuel comprises a hydrocarbon.

12. The method of claim 1, wherein the membrane comprises an electronically conducting phase and an ionically conducting phase.

13. The method of claim 12, wherein the electronically conducting phase comprises doped lanthanum chromite or an electronically conductive metal or combination thereof; and wherein the ionically conducting phase comprises a material selected from the group consisting of gadolinium or samarium doped ceria, yttria-stabilized zirconia (YSZ), lanthanum strontium gallate magnesite (LSGM), scandia-stabilized zirconia (SSZ), Sc and Ce doped zirconia (SCZ), and combinations thereof.

14. The method of claim 1, wherein the membrane comprises CoCGO or LST (lanthanum-doped strontium titanate)-stabilized zirconia.

15. The method of claim 14, wherein the stabilized zirconia comprises YSZ or SSZ or SCZ (scandia-ceria-stabilized zirconia), and wherein the LST comprises $LaSrCaTiO_3$.

16. The method of claim 1, wherein the membrane comprises Nickel, Copper, Cobalt, or Niobium-doped zirconia.

17. The method of claim 1, wherein the cathode exhaust is passed through a separator, wherein the generated carbon monoxide and hydrogen are separated from the exhaust.

18. The method of claim 17 comprising utilizing the separated CO and $H_2$ to produce methanol, ethanol, hydrocarbons, plastic monomers, polyethylene, or combinations thereof.

19. The method of claim 1, wherein the reactor comprises no interconnect and no current collector.

* * * * *